(12) United States Patent
Proudfoot et al.

(10) Patent No.: US 7,476,381 B2
(45) Date of Patent: Jan. 13, 2009

(54) METHODS OF REDUCING SERUM ALANINE TRANSFERASE LEVELS IN A SUBJECT WITH HEPATITIS

(75) Inventors: Amanda Proudfoot, Chens sur Leman (FR); Maureen Ajuebor, Calgary (CA); Mark Swain, Calgary (CA)

(73) Assignee: Laboratoires Serono SA, Coinsins, Vaud (CH)

( * ) Notice: Subject to any disclaimer, the term of this patent is extended or adjusted under 35 U.S.C. 154(b) by 80 days.

(21) Appl. No.: 10/540,234

(22) PCT Filed: Dec. 22, 2003

(86) PCT No.: PCT/EP03/51090

§ 371 (c)(1),
(2), (4) Date: Apr. 17, 2006

(87) PCT Pub. No.: WO2004/062688

PCT Pub. Date: Jul. 29, 2004

(65) Prior Publication Data

US 2006/0228327 A1 Oct. 12, 2006

(30) Foreign Application Priority Data

Dec. 23, 2002 (EP) .................................. 02102885
Jul. 17, 2003 (EP) .................................. 03077237

(51) Int. Cl.
*A61K 38/19* (2006.01)
*C07K 14/52* (2006.01)
(52) U.S. Cl. .................... 424/85.1; 514/12; 530/351
(58) Field of Classification Search ................... None
See application file for complete search history.

(56) References Cited

U.S. PATENT DOCUMENTS

| 5,739,103 A | 4/1998 | Rollins et al. |
| 5,965,697 A | 10/1999 | Czaplewski et al. |
| 2005/0053603 A1 | 3/2005 | Egashira et al. |

FOREIGN PATENT DOCUMENTS

| EP | 1 325 751 A1 | 7/2003 |
| WO | WO 96/38559 A1 | 12/1996 |
| WO | WO 98/13495 A1 | 4/1998 |
| WO | WO 02/028419 A2 | 4/2002 |
| WO | WO 02/30464 | 4/2002 |
| WO | WO 03/051921 A1 | 6/2003 |

OTHER PUBLICATIONS

Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-133.*
Doerks et al., Protein annotation: detective work for function prediction, 1998, Trends in Genetics, vol. 14, pp. 248-250.*
Ngo et al., The protein folding problem and tertiary structure prediction, 1994, pages 492-495.*
Skolnick et al., From genes to protein structure and function: novel applications of computational approaches in the genomic era, 2000, Trends in Biotech, vol. 18, Issue 1, pp. 34-39.*
Smith et al., The challenge of genome sequence annotation or "the devil is in the details", 1997, Nature Biotechnology, vol. 15, pp. 1222-1223.*
Wells et al., Addivity of mutational effects in proteins, 1990, Biochemistry, vol. 29, pp. 8509-8517.*
Proudfoot et al., The Journal of Biological Chemistry, 2001, vol. 276, Issue 14, pages 10620-10626.*
Christen et al., Animal models for autoimmune hepatitis, 2007, Autoimmune reviews, vol. 6, pp. 306-311.*
Washington, Autoimmune liver disease: overlap and outliers, 2007, Modern Pathology, vol. 20, pp. S15-S30.*
Database WPI, Section Ch, Week 200242, Accession No. 2002-394437, XP002238282, Apr. 18, 2002.
Laurence, J. S. et al. "Importance of basic residues and quaternary structure in the function of MIP-1beta: CCR5 binding and cell surface sugar interactions" *Biochemistry*, Apr. 24, 2001, pp. 4990-4999, vol. 40, No. 16.
Koopmann, W. et al. "Identification of a glycosaminoglycan-binding site in chemokine macrophage inflammatory protein-1-alpha" *Journal of Biological Chemistry*, Apr. 11, 1997, pp. 10103-10109, vol. 272, No. 15.
Fisher, N.C. et al. "Serum concentrations and peripheral secretion of the beta chemokines monocyte chemoattractant protein 1 and macrophage inflammatory protein 1alpha in alcoholic liver disease" *Gut*, 1999, pp. 416-420, vol. 45, No. 3.
Miyaguchi, S. et al. "Elevated plasma RANTES in primary biliary cirrhosis patients" *Hepatology Research*, 1997, pp. 156-163, vol. 8, No. 3.
Ajuebor, M. et al. "Novel protective effects of the CC chemokine CCL2/MCP-1 in concanavalin A-induced acute hepatitis" *Gastroenterology*, Apr. 2002, p. A-637, vol. 122, No. 4, Suppl.1, abstract only.
Ajuebor, M. et al. "The coordinated action of CC chemokines and their receptors may orchestrate hepatic inflammation during chronic experimental cholangitis" *Gastroenterology*, Jul. 2002, p. 57, vol. 123, No. 1, Suppl., abstract only.
Ajuebor, M. et al. "CCL3/MIP-1 alpha, a crucial chemokine in the pathogenesis of T-cell mediated hepatitis in mice" *Biosis*, Mar. 2003, pp. 1-2, XP002263040.
Proudfoot, A. E. I. et al. "Strategies for chemokine antagonists as therapeutics" *Seminars in Immunology*, 2003, pp. 57-65, vol. 15, No. 1.

\* cited by examiner

*Primary Examiner*—Robert Landsman
*Assistant Examiner*—Ian Dang
(74) *Attorney, Agent, or Firm*—Saliwanchik, Lloyd & Saliwanchik (57) ABSTRACT

CC-Chemokine mutants having reduced Glycosaminoglycans (GAG)-binding properties are effective against liver fibrotic inflammatory and/or autoimmune diseases. Particularly preferred are the mutants of CCL5/RANTES having reduced GAG-binding properties.

6 Claims, 3 Drawing Sheets

SEQUENCE LISTING

<160> NUMBER OF SEQ ID NOS: 3

<210> SEQ ID NO 1
<211> LENGTH: 68
<212> TYPE: PRT
<213> ORGANISM: artificial sequence
<220> FEATURE:
<223> OTHER INFORMATION: Triple 40's RANTES mutant

<400> SEQUENCE: 1

```
Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Ala Ala Asn Ala Gln
        35                  40                  45

Val Cys Ala Asn Pro Glu Lys Lys Trp Val Arg Glu Tyr Ile Asn Ser
    50                  55                  60

Leu Glu Met Ser
65
```

<210> SEQ ID NO 2
<211> LENGTH: 70
<212> TYPE: PRT
<213> ORGANISM: artificial sequence
<220> FEATURE:
<223> OTHER INFORMATION: Triple MIP-1alpha mutant

<400> SEQUENCE: 2

```
Ala Ser Leu Ala Ala Asp Thr Pro Thr Ala Cys Cys Phe Ser Tyr Thr
1               5                   10                  15

Ser Ala Gln Ile Pro Gln Asn Phe Ile Ala Asp Tyr Phe Glu Thr Ser
            20                  25                  30

Ser Gln Cys Ser Lys Pro Gly Val Ile Phe Leu Thr Lys Ala Ser Ala
        35                  40                  45

Gln Val Cys Ala Asp Pro Ser Glu Glu Trp Val Gln Lys Tyr Val Ser
    50                  55                  60

Asp Leu Glu Leu Ser Ala
65                  70
```

```
<210> SEQ ID NO 3
<211> LENGTH: 69
<212> TYPE: PRT
<213> ORGANISM: artificial sequence
<220> FEATURE:
<223> OTHER INFORMATION: Triple MIP-1beta mutant

<400> SEQUENCE: 3

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
            20                  25                  30

Ser Leu Cys Ser Gln Pro Ala Val Val Phe Gln Thr Ala Ala Ser Ala
        35                  40                  45

Gln Val Cys Ala Asp Pro Ser Glu Ser Trp Val Gln Glu Tyr Val Tyr
    50                  55                  60

Asp Leu Glu Leu Asn
65
```

METHODS OF REDUCING SERUM ALANINE TRANSFERASE LEVELS IN A SUBJECT WITH HEPATITIS

CROSS-REFERENCE TO RELATED APPLICATION

This application is the U.S. national stage application of International Patent Application No. PCT/EP2003/051090, filed Dec. 22, 2003, the disclosure of which is hereby incorporated by reference in its entirety, including all figures, tables and amino acid or nucleic acid sequences.

FIELD OF THE INVENTION

The present invention relates to novel therapeutic applications of CC-chemokine mutants having a reduced GAG-binding activity.

BACKGROUND OF THE INVENTION

Chemokines are secreted pro-inflammatory proteins of small dimensions (70-130 amino acids) mostly involved in the directional migration and activation of cells, especially the extravasation of leukocytes from the blood to tissue localizations needing the recruitment of these cells (Baggiolini M et al., 1997; Rossi D and Zlotnik A, 2000; Fernandez E J and Lolis E, 2002). Usually chemokines are produced at the site of an injury, inflammation, or other tissue alteration in a paracrine or autocrine fashion, triggering cell-type specific migration and activation.

Depending on the number and the position of the conserved cysteines in the sequence, chemokines are classified into C-, CC-, CXC- and $CX_3C$-chemokines. Inside each of these families, chemokines can be further grouped according to the homology of the entire sequence, or of specific segments.

A series of heptahelical G-protein coupled membrane receptors, are the binding partners that allow chemokines to exert their biological activity on the target cells, which present specific combinations of receptors according to their state and/or type. An unified nomenclature for chemokine ligands and receptors, which were originally named by the scientists discovering them in a very heterogeneous manner, has been proposed to associate each of these molecule to a systemic name including a progressive number CCL1, CCL2, etc. for CC-chemokines; CCR1, CCR2, etc. for CC-chemokines receptors, and so on.

The physiological effects of chemokines result from a complex and integrated system of concurrent interactions. The receptors often have overlapping ligand specificity, so that a single receptor can bind different chemokines, as well a single chemokine can bind different receptors. In particular, N-terminal domain of chemokines is involved in receptor binding and N-terminal processing can either activate chemokines or render chemokines completely inactive.

Amongst all the chemokines characterized so far, CC-chemokines, such as CCL5 (also known as RANTES; Appay V and Rowland-Jones S L, 2001) or CCL3 (also known as MIP-1alpha, U.S. Pat. No. 6,355,476), have been intensively studied to identify therapeutically useful molecules. Variants of CC-chemokines, missing up to nine N-terminal amino acids, have been tested for their activity as inhibitors or antagonists of the naturally occurring forms. These molecules are inactive on monocytes and are useful as receptor antagonists (Gong J H et al., 1996; WO 99/16877). Alternatively, N-terminal extension of the mature CC-chemokine with one Methionine results in almost complete inactivation of the molecule, which also behaves as an antagonist for the authentic one (WO 96/17935).

Moreover, in order to perform structure-function analysis of CC-chemokines, variants containing substitutions or chemical modifications in different internal positions, as well as CC-chemokine derived peptides, have been tested for the interactions with receptors or other molecules. Some of these variants have been disclosed as having significatively altered binding properties, and sometimes they are active as CC-chemokine antagonists, having potential therapeutic applications in the treatment of HIV infection and some inflammatory or allergic diseases (WO 99/33989; Nardese V et al., 2001). In particular, the binding determinants and the physiological relevance of the interactions of chemokines, by the means of specifically positioned basic residues, with Glycosaminoglycans (GAGs) has been intensively studied (WO 02/28419; Vives R et al., 2002; McCornack M A et al., 2003; Stringer S E et al., 2002; Fukui S et al., 2002; Laurence J S et al., 2001; Martin L et al., 2001; Koopmann W and Krangel M S, 1997).

Even though there are potential drawbacks in using chemokines as therapeutic agents (tendency to aggregate, promiscuous binding), these molecules offer the possibility for therapeutic intervention in pathological conditions associated to such processes, in particular by inhibiting/antagonizing specific chemokines and their receptors at the scope to preventing the excessive recruitment and activation of cells, in particular leukocytes, for a variety of indications related to inflammatory and autoimmune diseases, cancers, and bacterial or viral infections (Schneider G P et al., 2001, Baggiolini M, 2001; Godessart N and Kunkel S L, 2001).

The possible therapeutic applications of chemokine-related compounds against hepatic diseases have been intensively studied, as recently reviewed (Ajuebor M N et al., 2002; Marra F, 2002, Colletti L M, 1999). In particular, liver specific inflammation is mediated by activated CD4(+) T cells and driven by an upregulation of the hepatic expression of IFNgamma, but the mechanisms governing T cell migration from the blood into tissues during T cell-mediated hepatitis remains incompletely understood, since the endogenous mediators that promote the recruitment of T cells to the liver during T cell-mediated liver diseases have been poorly characterized.

It has been demonstrated that some chemokines are highly expressed and important for the recruitment for liver-infiltrating lymphocytes in hepatitis-related animal models (acetaminophen-induced, Concanavalin A-induced, adenovirus-induced, or hepatitis B virus-specific), suggesting a specific role of these molecules in the development of hepatitis (Bautista A P, 2002; Lalor P F et al., 2002; Hogaboam C M et al., 2000; Kusano F et al., 2000).

Some broad spectrum CC-chemokine antagonists were disclosed in connection to hepatic diseases (WO 00/73327; WO 01/58916; U.S. Pat. No. 6,495,515). CXC chemokines are capable to induce rapid hepatocyte proliferation and liver regeneration after injury (WO 01/10899). CCR1 or MIP-1alpha antagonists can be used for inhibiting graft-related or ischemia/reperfusion-related liver dysfunctions (WO 00/44365; Murai M et al., 1999).

However, prior art fails to describe any therapeutic efficacy of an isolated, specific CC-chemokine mutant generated by the substitution of internal residues, against liver fibrotic inflammatory and/or autoimmune diseases.

SUMMARY OF THE INVENTION

It has been surprisingly found that a CCL5/RANTES mutant having reduced GAG-binding properties, resulting from the substitution of specific internal residues, counteracts liver fibrotic injury in a relevant animal model.

These evidences demonstrate the possibility of using this and other mutants of CC-chemokines (such as CCL3/MIP-1alpha or CCL4/MIP-1beta) having similar reduced GAG-binding activity in the treatment of liver fibrotic inflammatory and/or autoimmune diseases. Particularly preferred are CCL5 mutants are the GAG-binding defective mutants of CCL5 generated by appropriately mutagenising the GAG-binding domain of CCL5.

Other features and advantages of the invention will be apparent from the following detailed description.

DETAILED DESCRIPTION OF THE INVENTION

The main object of the present invention is the use of a CC-chemokine mutant having a reduced GAG-binding activity for the treatment of liver fibrotic inflammatory and/or autoimmune diseases. In particular, such mutants are the ones already disclosed in the prior art for the CC-chemokines CCL3/MIP-1alpha, CCL4/MIP-1beta, or CCL5/RANTES (WO 02/28419; Laurence J S et al., 2001; Koopmann W and Krangel M S, 1997).

In particular, the CC-chemokine mutants have the sequence of the ones disclosed in the prior art under the names of triple 40's RANTES mutant (SEQ ID NO: 1), triple MIP-1alpha mutant (SEQ ID NO: 2), and triple 40's MIP-1beta mutant (SEQ ID NO: 3) mutants. It is however evident that any other corresponding mutant of CCL3/MIP-1alpha, CCL4/MIP-1beta, or CCL5/RANTES having reduced GAG-binding properties resulting from the substitution of the same residues disclosed in the prior art but with a different amino acid (i.e. the basic residue is substituted with a non-polar amino acid other than Ala or with an acid residue), or resulting from a substitution in other position(s) can be used according to the invention.

These polypeptides can be prepared by chemical synthesis, by site-directed mutagenesis techniques, or any other known technique suitable thereof, which provide a finite set of substantially corresponding mutated or shortened peptides or polypeptides which can be routinely obtained and tested by one of ordinary skill in the art using the teachings presented in the prior art and in the Examples of the present patent application. Similar compounds may also result from conventional mutagenesis technique of the encoding DNA, from combinatorial technologies at the level of encoding DNA sequence (such as DNA shuffling, phage display/selection), or from computer-aided design studies based on the tridimensional structure and other functional assays of chemokines, with or without the presence of GAGs (Rajarathnam K, 2002; Vives R et al., 2002; McCornack M A et al., 2003; Stringer S E et al., 2003; Fukui S et al., 2002; Martin L et al., 2001).

The above cited prior art on GAG-binding defective CC-chemokine mutants fails to identify liver fibrotic inflammatory and/or autoimmune diseases as therapeutic indications in which these molecules can provide a beneficial effect. As there are currently therapies only partially effective and/or acceptable for treating diseases such as alcoholic liver diseases, viral or autoimmune hepatitis, the disclosed CC-chemokine mutants represent alternative therapeutic compounds possibly better accepted and efficient than the current therapies The wording "a reduced GAG-binding activity" or "GAG-binding defective" means that the CC-chemokine mutants have a lower ability to bind to GAGs, i.e. a lower percentage of each of these mutants bind to GAGs (like heparin sulphate) with respect to the corresponding wild-type molecule, as measured with the assays in the above cited prior art disclosing such mutants.

In addition to the mutation at the specific positions leading to the decreased affinity for GAGs, the CC-chemokine mutants may include other modifications with respect to the wild-type molecule, generating active variants of said CC-chemokine mutants in which one or more amino acids have been added, deleted, or substituted in a conservative manner. These additional modifications should be intended to maintain, or even improve, the properties of the specific mutants, or by any other relevant means known in the art, making them equally useful for treating liver fibrotic inflammatory and/or autoimmune diseases. Other additional preferred changes in these active variants are commonly known as "conservative" or "safe" substitutions, that is, with amino acids having sufficiently similar chemical properties, in order to maintain the structure and the biological function of the CC-chemokine mutant. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The synonymous amino acid groups and more preferred synonymous groups are those defined in Table I.

Alternatively, active CC-chemokine mutants may contain on or more non-natural, amino acid derivatives being "synonymous" to a natural amino acid, are those defined in Table II. By "amino acid derivative" is intended an amino acid or amino acid-like chemical entity other than one of the 20 genetically encoded naturally occurring amino acids. In particular, the amino acid derivative may contain substituted or non-substituted alkyl linear, branched, or cyclic moieties, and may include one or more heteroatoms. The amino acid derivatives can be made de novo or obtained from commercial sources (Calbiochem-Novabiochem AG, Switzerland; Bachem, USA). Various methodologies for incorporating unnatural amino acids derivatives into proteins, using both in vitro and in vivo translation systems, to probe and/or improve protein structure and function are disclosed in the literature (Dougherty D A, 2000).

The term "active" means that such alternative compounds should maintain the therapeutic properties of the CC-chemokines mutants against liver fibrotic inflammatory and/or autoimmune diseases as described in the present invention, and should be as well pharmaceutically acceptable and useful.

In another embodiment, a polypeptide comprising the GAG-binding defective CC-chemokine mutant and an amino acid sequence belonging to a protein sequence other than the corresponding CC-chemokine can be also used for treating liver fibrotic inflammatory and/or autoimmune diseases. The heterologous sequence is intended provide additional properties without considerably impairing the therapeutic activity. Examples of such additional properties are an easier purification procedure, a longer lasting half-life in body fluids, an additional binding moiety, the maturation by means of an endoproteolytic digestion, or extracellular localization. This latter feature is of particular importance for defining a specific group of fusion or chimeric proteins included in the above definition since it allows the CC-chemokine mutants to be localized in the space where not only where the isolation and purification of these polypeptides is facilitated, but also where CC-chemokines naturally interact with receptors and other molecules. Design of the moieties, ligands, and linkers, as well methods and strategies for the construction, purification, detection and use of fusion proteins are widely discussed in the literature (Nilsson J et al., 1997; "Applications of chimeric genes and hybrid proteins" Methods Enzymol. Vol. 326-328, Academic Press, 2000; WO 01/77137).

Additional protein sequences can be chosen amongst extracellular domains of membrane-bound protein, immunoglobulin constant regions, multimerization domains, extracellular proteins, signal peptide-containing proteins, export signal-containing proteins. The choice of one or more of these sequences to be fused to the CC-chemokine mutants is functional to the desired use, delivery and/or preparation method.

The GAG-binding defective CC-chemokine mutants can be also provided for the treatment of liver fibrotic inflammatory and/or autoimmune diseases in the form of the corresponding active precursor, salt, derivative, conjugate or complex. These alternative forms may be preferred according to the desired method of delivery and/or production.

The "precursors" are compounds which can be converted into other compounds by metabolic and enzymatic processing prior or after the administration to the cells or to the organism.

The term "salts" herein refers to both salts of carboxyl groups and to acid addition salts of amino groups of the peptides, polypeptides, or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the original polypeptide.

The term "fractions" as herein used refers to derivatives which can be prepared from the functional groups present on the lateral chains of the amino acid moieties or on the N-/ or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups. Alternatively, the derivatives may contain sugars or phosphates groups linked to the functional groups present on the lateral chains of the amino acid moieties. Such molecules can result from in vivo or in vitro processes which do not normally alter primary sequence, for example chemical derivativization of peptides (acetylation or carboxylation), phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes).

The term "derivatives" as herein used refers to derivatives which can be prepared from the functional groups present on the lateral chains of the amino acid moieties or on the N- or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Alternatively, useful conjugates or complexes of the CC-chemokine mutants can be generated by using molecules and methods known in the art for improving the detection of the interaction with other proteins (radioactive or fluorescent labels, biotin), therapeutic efficacy (cytotoxic agents, isotopes), or drug delivery efficacy, such as polyethylene glycol and other natural or synthetic polymers (Pillai O and Panchagnula R, 2001). In the latter case, a site-directed modification of an appropriate residue, present in the natural sequence or introduced by mutating the natural sequence, at an internal or terminal position, can be introduced. Similar modifications have been already disclosed for chemokines (WO 02/04499; WO 02/04015; Vita C et al., 2002).

Any residue can be used for attachment, provided it has a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment. Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly(N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the N-terminal region of a protein. Such modification acts to provide the protein in a "pro-drug" form that, upon degradation of the linker, releases the protein without polymer modification.

The GAG-binding defective CC-chemokine mutants may be prepared by any appropriate procedure in the art, such as recombinant DNA-related technologies involving the expression in Eukaryotic cells (e.g. yeasts, insect or mammalian cells) or Prokaryotic cells. Detailed methods for producing the GAG-binding defective CC-chemokine mutants can be found in the prior art originally disclosing them (WO 02/28419; Laurence J S et al., 2001; Koopmann W and Krangel M S, 1997), as well as in other literature featuring protocols for chemokine production (Edgerton M D et al., 2000) or common molecular biology techniques for the production of recombinant proteins in Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Alternatively the GAG-binding defective CC-chemokine mutants may be prepared by any other well known procedure in the art, in particular, by the well established chemical synthesis procedures, which can be efficiently applied on these molecule given the short length. Totally synthetic chemokines, also containing additional chemical groups, are disclosed in the literature (Brown A et al., 1996; Vita C et al., 2002).

Examples of chemical synthesis technologies are solid phase synthesis and liquid phase synthesis. As a solid phase synthesis, for example, the amino acid corresponding to the N-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After the synthesis, the desired peptide is subjected to the de-protection reaction and cut out from the solid support. Such peptide cutting reaction may be carried with hydrogen fluoride or tri-fluoromethane sulfonic acid for the Boc method, and with TFA for the Fmoc method. Finally, the intact full-length peptides are purified and chemically or enzymatically folded (including the formation of disulphide bridges between cysteines) into the corresponding CC-chemokine mutants.

Purification of the natural, synthetic or recombinant proteins is carried out by any one of the methods known for this purpose, i.e. any conventional procedure involving extraction, precipitation, chromatography, electrophoresis, or the like. A further purification procedure that may be used in preference for purifying the protein is affinity chromatography using monoclonal antibodies, heparin, or any other suitable ligand that can bind the target protein at high efficiency and can be immobilized on a gel matrix contained within a column. Impure preparations containing the proteins are passed through the column. The protein will be bound to the column by means of this ligand while the impurities will pass through. After washing, the protein is eluted from the gel by a change in pH or ionic strength. Alternatively, HPLC (High Performance Liquid Chromatography) can be also used.

Another object of the present invention is the use of a CC-chemokine mutant, wherein the CC-chemokine is CCL3/MIP-1alpha, CCL4/MIP-1beta, or CCL5/RANTES, having reduced GAG-binding activity in the preparation of a pharmaceutical composition for liver inflammatory and/or fibrotic diseases, in particular when formulated in combination with pharmaceutically acceptable carriers, excipients, stabilizers, adjuvants, or diluents.

A non-limitative list of disorders involving hepatic damage in which the CC-chemokine mutant having reduced GAG-binding activity can be used includes alcoholic liver diseases (cirrohosis, steatosis), a viral hepatitis, an autoimmune hepatitis, or any other liver fibrotic degeneration.

Still another object of the present invention are methods for the treatment or prevention of a liver inflammatory and/or fibrotic disease, comprising the administration of an effective amount of a CC-chemokine mutant having reduced GAG-binding activity, wherein the CC-chemokine is CCL3/MIP-1alpha, CCL4/MIP-1beta, or CCL5/RANTES.

The CC-chemokine mutants may be used alone, or with another therapeutic composition acting synergically or in a coordinated/sequential manner with them in the treatment of liver inflammatory and/or fibrotic diseases. For example, similar synergistic properties of CC-chemokine mutants have been demonstrated in combination with cyclosporin (WO 00/16796).

In view of the claimed uses and methods of treatment, any drug delivery method allowing the targeting of the GAG-binding defective CC-chemokine mutant is preferred. Similar methods are known in the prior and may involve the conjugation of the CC-chemokine mutant with galactosylated or mannosylated albumin (Chuang V T et al., 2002) or the synthesis of polymeric nanoparticles from a sugar-containing conjugate composed of lactobionic acid, diamine-terminated polyethylene glycol) and cholic acid (Kim I S and Kim S H, 2002).

An "effective amount" refers to an amount of the active ingredients that is sufficient to affect the course and the severity of the disease, leading to the reduction or remission of the liver pathology. The effective amount will depend on the route of administration and the condition of the patient.

The pharmaceutical compositions may be formulated in any acceptable way to meet the needs of the mode of administration for treating liver diseases. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soy bean oil, mineral oil, sesame oil). For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives that may facilitate the processing of the active compounds into preparations which can be used pharmaceutically. Moreover, these compositions may contain another active ingredient that can act synergically or in a coordinated manner with the CC-chemokine mutants.

The administration of such active ingredient may be by intravenous, intramuscular or subcutaneous route. Other routes of administration, which may establish the desired effects of the respective ingredients in the liver, are comprised by the present invention. For example, administration may be by various parenteral routes such as subcutaneous, intravenous, intradermal, intramuscular, intraperitoneal, intranasal, transdermal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

The optimal dose of active ingredient may be appropriately selected according to the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

Usually a daily dosage of active ingredient can be about 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

The present invention has been described with reference to the specific embodiments, but the content of the description comprises all modifications and substitutions, that can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Efficacy of Different CCL5 Mutant Having a Reduced GAG-binding Activity in a Hepatitis Model Concanavalin A (Con A)-induced liver injury depends on the activation of recruitment of CD4(+) T cells by macrophages. In general, T cells are the driving force underlying immunologically mediated hepatic disorders, making therefore the Con-A model highly relevant for studying the pathophysiology of diseases such as autoimmune or acute hepatitis (Takeda K et al., 2000; Tiegs G et al., 1992).

The assay involves the measurement of serum alanine aminotransferase (ALT), a liver enzyme contained in hepatocytes and released into serum when these cells are damaged. ALT is the most widely used marker in humans and animals to document damage and destruction of liver cells (as in hepatitis), and, generally, ALT concentration correlates with histological changes.

As example of CC-chemokine mutant having a reduced GAG-binding activity, the CCL5 mutant called triple 40's RANTES mutant was chosen and expressed in *E. coli* and purified as previously described (WO 02/28419).

Specific pathogen-free male C57BL/6 mice (body weight of 21-23 grams; Charles River Breeding Farms) were treated with Phosphate Buffer Saline (PBS; vehicle control; 0.1 ml), or with one of above described CCL5 mutants (30 micrograms/mouse in 0.1 ml PBS). The mice (5-10 per group) were injected s.c. 1 hour prior to Con-A i.v. injection (freshly prepared Con A type V, 0.25 mg/mouse in 0.1 ml PBS; Sigma). At 8 hours after Con A administration and under halothane anaesthesia, blood was collected for measuring plasma ALT using a commercial kit for ALT determination (Sigma).

Figure 1:
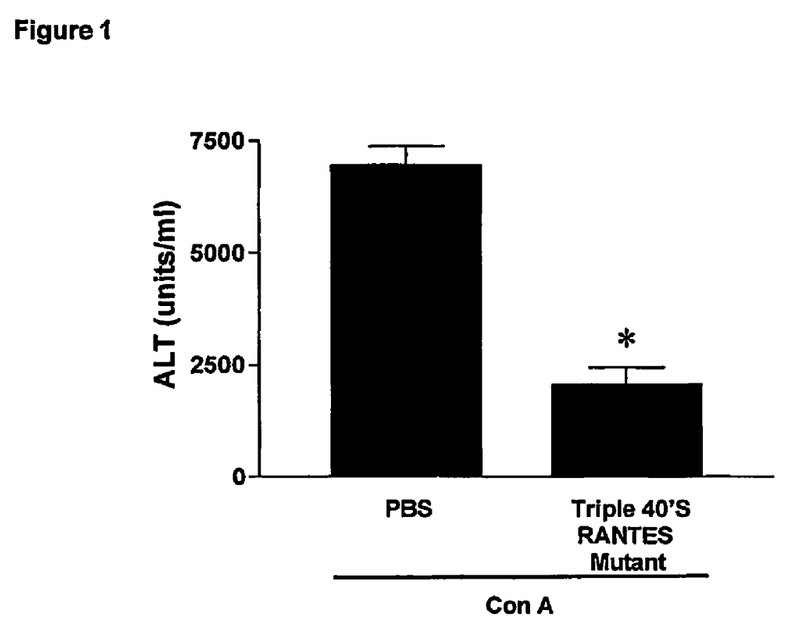
FIG. 1: effect of the treatment with a GAG-binding defective CCL5 mutant (triple 40's RANTES mutant) in an animal model for liver diseases based on Concanavallin A (Con A) administration and measurement of serum alanine transaminase (ALT). The asterisk indicates the statistical significance of the measured difference (P<0.05) when compared to the PBS-treated controls.

This biochemical approach for quantifying liver injury showed that the triple 40's RANTES mutant is capable of reducing ALT concentration in serum of the pre-treated animals in a statistically significant manner (FIG. 1).

Example 2

Relevance of MIP-1alpha Expression in the Concanavallin A Mouse Models

A time course experiments on normal mice was performed to verify if there is any correlation between ALT levels and hepatic CCL3/MIP-1alpha protein concentration in control male C57BL/6J mice and CCL3/MIP-1alpha knock-out C57BL/6J (Cook D N et al., 1995).

Mice (body weight of 21-23 grams; 5-6 weeks old; commercially available through Jackson Laboratories and Charles River Breeding Farms) were injected intravenously with freshly prepared Concanavallin A (Con A; 13.5 mg/kg; Sigma) in 0.1 ml Phosphate Buffer Saline (PBS), or with 0.1 PBS only (vehicle control).

The levels of serum alanine transaminase (ALT) were measured using a commercial kit (Sigma). Blood was collected from mice at 30 minutes, 90 minutes, 8 hours and 24 hours after Con A administration and under halothane anesthesia.

In a separate set of experiments, the levels of hepatic CCL3/MIP-1alpha or IFNgamma were determined in control and CCL3/MIP-1alpha knock-out mice that were injected with Con A or PBS only. Mice were sacrificed at the indicated time points after Con A or PBS injection and livers were perfused with ice-cold sterile PBS to remove blood elements. Individual perfused livers were homogenised in ice-cold PBS buffer containing protease cocktail inhibitor (Sigma) immediately after their removal, tissue homogenates were centrifuged twice, and the supernatants filtered through a 0.45-mm filter and stored at −80° C. until used for protein determination. Hepatic CCL3/MIP-1alpha and IFNgamma levels were measured by specific murine ELISA following a published protocol (Bone-Larson C L et al., 2001), and using commercial antibodies (R&D Systems). Total protein concentration in the homogenates was calculated using a commercial protein colorimetric assay (Bio-Rad Laboratories).

Figure 2:
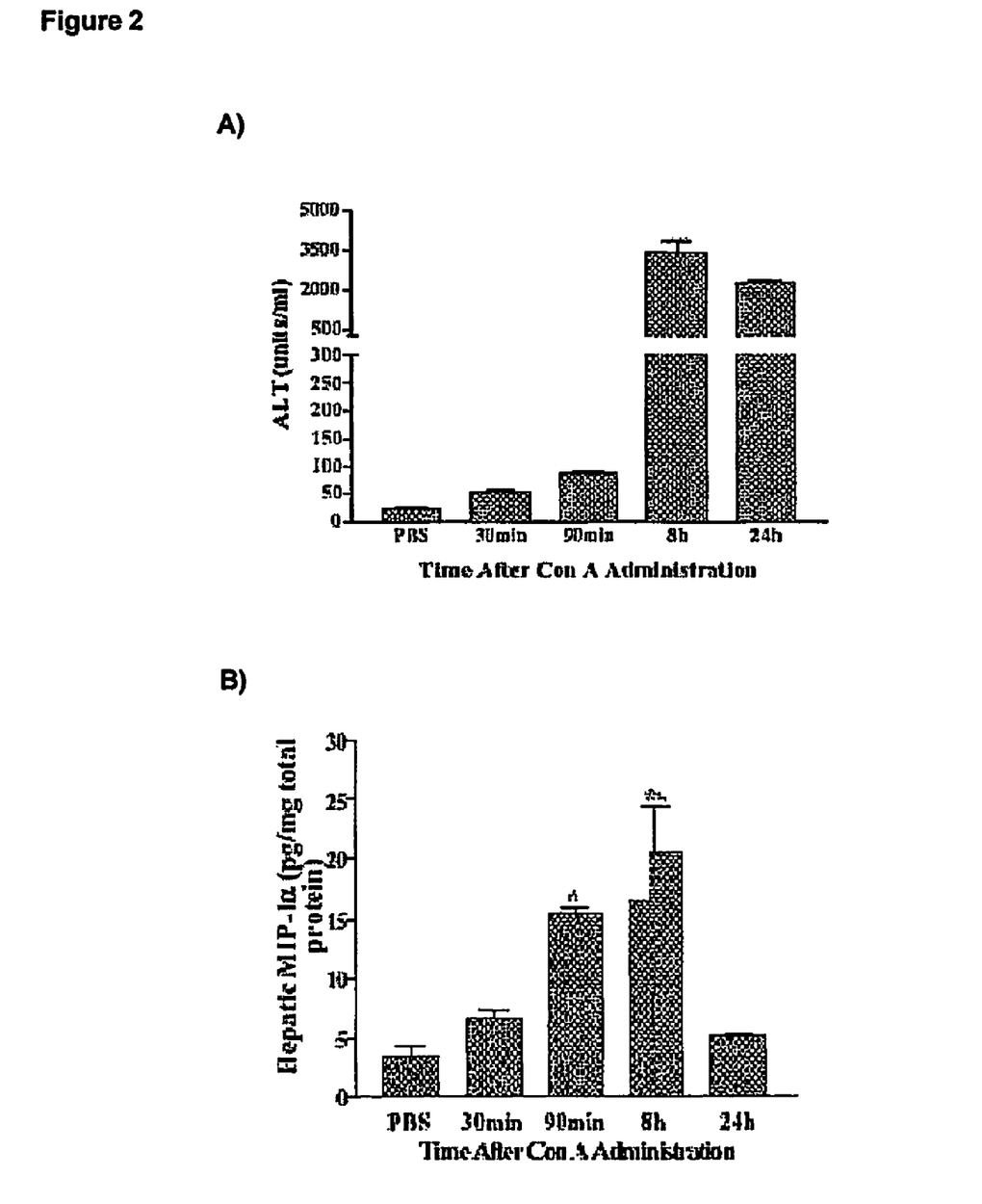
FIGS. 2A-B: time course analysis of the effect of Con A (Con A) administration on serum ALT (A) and on hepatic MIP-1alpha (B) levels in mice.

The data demonstrated that maximum hepatic injury, as evaluated by using ALT concentration, and peak hepatic CCL3/MIP-1alpha levels can be both observed at 8 hours after intravenous administration of a single dose of Con A (13.5 mg/kg). This compound caused a more than 100-fold increase of ALT levels (FIG. 2A) paralleled by a more than five-fold increase of hepatic CCL3/MIP-1alpha protein expression (FIG. 2B) above control PBS injection.

Figure 3:
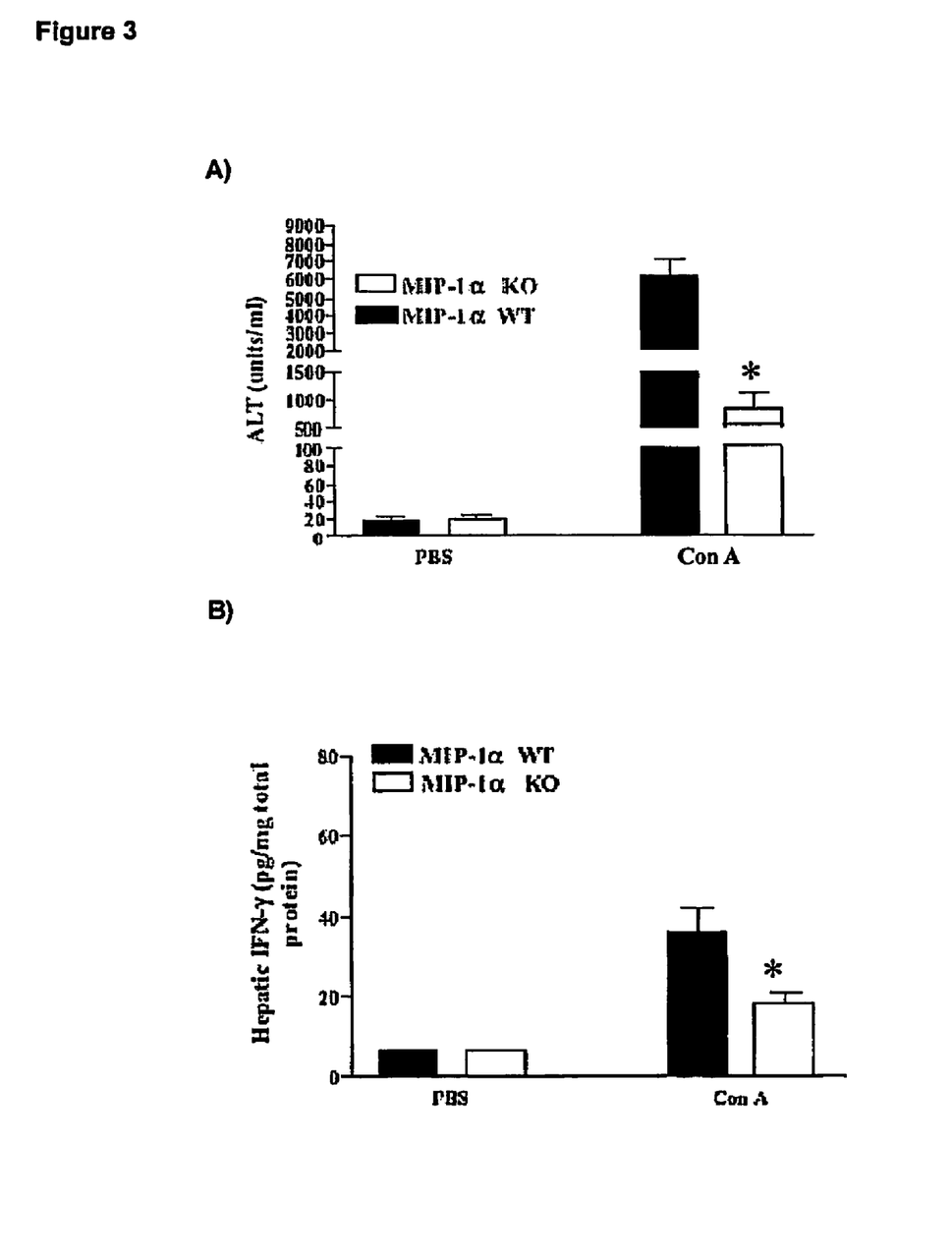
FIGS. 3A-B: effect of the treatment with Con A or PBS on control (MIP-1α WT) and MIP-1alpha knock-out (MIP-1α KO) mice on serum ALT (A) or hepatic IFN-gamma (B) levels in mice. The levels were measured 8 hours after the administration of PBS or Con A. The asterisk indicates the statistical significance of the measured difference (P<0.05) when compared to the PBS-treated controls.

The effect of Con A administration in transgenic mice lacking the CCL3/MIP-1alpha gene to verify if CCL3/MIP-1 alpha deficiency impairs the development of Con A-induced hepatic injury. In fact, CCL3/MIP-1alpha knock-out mice exhibited significantly less hepatic injury 8 hours after the Con A injection relative to control m ice, as demonstrated biochemically by a significant reduction (approx. five-fold) in ALT level (FIG. 3A). Moreover, hepatic concentration of IFNgamma, one of the cytokines implicated in the pathogenesis of Con A-induced hepatitis since it is produced by CD4 (+) T cells recruited to the liver (Mizuhara H et al., 1996), is significantly lowered in CCL3/MIP-1alpha knock-out mice at 8 hours after Con A administration, when compared to control mice (FIG. 3B).

All data are shown as Mean±Standard Deviation. For comparisons of means between 2 experimental groups (n=4-10 mice per group) a Student's unpaired t-test was used, considering P value <0.05 statistically significant Statistical analyses were performed using GraphPad Instat (version 3.00) Software.

The analysis of the data generated with the substituted CCL5 mutant and in MIP-alpha knock-out mice demonstrate how, using a single CC-chemokine mutant having the specific binding profile characterized in the prior art (WO 02/28419; Laurence J S et al., 2001; Koopmann W and Krangel M S, 1997), a surprising therapeutically relevant effect can be obtained, suggesting the use of similar molecules in the treatment of fibrotic liver diseases involving inflammatory and/or autoimmunitary reactions. The comparison with results obtained using other animal models for such diseases (acetaminophen-induced or adenovirus-induced hepatitis), may provide further confirmation of the therapeutic applicability of these specific CC-chemokine mutants.

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S-Me-Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

REFERENCES

Ajuebor M N et al., Biochem Pharmacol 2002, 63:1191-6.
Appay V and Rowland-Jones S L, Trends Immunol 2001, 22: 83-7.
Baggiolini M et al., Annu Rev Immunol 1997, 15: 675-705.
Baggiolini M, J Intern Med 2001, 250: 91-104.
Bone-Larson C L et al., J Immunol 2001, 167: 7077-83.
Brown A et al., J Pept Sci 1996, 2: 40-6.
Bautista A P, Front Biosci 2002, 7: a117-25.
Chuang V T et al., Pharm Res 2002, 19: 569-77.
Cleland J L et al., Curr Opin Biotechnol 2001, 12: 212-9.
Colletti L M, Drug News Perspect 1999, 12: 5-11.
Cook D N et al., Science 1995, 269:1583-1585.
Dougherty D A, Curr Opin Chem Biol 2000, 4: 645-52.
Edgerton M D et al., Methods Mol Biol 2000, 138: 33-40.

Fernandez E J and Lolis E, Annu Rev Pharmacol Toxicol 2002, 42:469-499.
Fukui S et al., Nat Biotechnol 2002, 20: 1011-7.
Godessart N and Kunkel S L, Curr Opin Immunol 2001, 13: 670-675.
Gong J H et al., J Biol Chem 1996, 271: 10521-7.
Hogaboam C M et al., Am J Pathol 2000, 156: 1245-52.
Kim I S and Kim S H, Int J Pharm 2002, 245: 67-73.
Koopmann Wand Krangel M S, J Biol Chem 1997, 272: 10103-9.
Kusano F et al., Lab Invest 2000, 80: 415-22.
Lalor P F et al., Immunol Cell Biol 2002, 80: 52-64.
Laurence J S et al., Biochemistry 2001, 40: 4990-9.
Luo B and Prestwich G D, Exp Opin Ther Patents 2001, 11: 1395-1410.
Marra F, Front Biosci 2002, 7: d1899-914.
Martin L et al., Biochemistry 2001, 40: 6303-18.
McCornack M A et al., J Biol Chem 2003, 278: 1946-56 (epub ahead of print on Oct. 30, 2002).
Mizuhara H et al., Hepatology 1996, 23: 1608-1615.
Murai M et al., J Clin Invest 1999, 104: 49-57.
Murphy L R et al., Protein Eng 2000, 13:149-52.
Nardese V et al., Nat Struct Biol 2001, 8: 611-5.
Nilsson J et al., Protein Expr Purif 1997, 11: 1-16.
Pillai O and Panchagnula R, Cur Opin Chem Biol 2001, 5: 447-451.
Rajarathnam K, Curr Pharm Des 2002, 8: 2159-69.
Rogov S I and Nekrasov A N, Protein Eng, 14: 459-463, 2001.
Rossi D and Zlotnik A, Annu Rev Immunol 2000, 18:217-42.
Schneider G P et al., Int J Mol Med 2001, 8: 235-44.
Stringer S E et al., Blood 2003, 101: 2243-5 (epub ahead of print on Oct. 24, 2002).
Takeda K et al., Proc Natl Acad Sci USA 2000, 97: 5498-503.
Tiegs G et al., J Clin Invest 1992, 90: 196-203.
Vita C et al., J Immunol Methods 2002, 266: 53-65.
Vives R et al., Biochemistry 2002, 41: 14779-89.

The invention claimed is:

1. A method for reducing serum alanine aminotransferase (ALT) in a subject with hepatitis comprising the administration of an effective amount of a CC-chemokine mutant comprising SEQ ID NO: 1 and having reduced glycosaminoglycan (GAG)-binding activity as compared to the wild type peptide to a subject with hepatitis.

2. The method according to claim 1, wherein the CC-chemokine mutant further comprises an immunoglobulin constant region.

3. The method according to claim 1, wherein the hepatitis is an autoimmune hepatitis.

4. The method according to claim 1, further comprising the measurement of serum ALT levels in said subject.

5. A method for reducing serum alanine aminotransferase (ALT) levels in a patient comprising measuring serum ALT levels in the patient and administering an effective amount of a CC-chemokine mutant comprising SEQ ID NO: 1 and having reduced glycosaminoglycan (GAG)-binding activity as compared to the wild type peptide to a patient.

6. The method according to claim 5, wherein the CC-chemokine mutant further comprises an immunoglobulin constant region.

* * * * *